United States Patent [19]

Bank et al.

[11] Patent Number: 5,596,120

[45] Date of Patent: Jan. 21, 1997

[54] PROCESS FOR PREPARATION OF ORGANOSILANES

[75] Inventors: Howard M. Bank, Freeland; Binh T. Nguyen, Midland, both of Mich.

[73] Assignee: Dow Corning Corporation, Midland, Mich.

[21] Appl. No.: 546,883

[22] Filed: Oct. 23, 1995

[51] Int. Cl.[6] .................................................. C07F 7/08
[52] U.S. Cl. .................................................. 556/480
[58] Field of Search .................................................. 556/480

[56] References Cited

U.S. PATENT DOCUMENTS

| | | | |
|---|---|---|---|
| 3,080,324 | 3/1963 | Richards | 149/36 |
| 3,801,558 | 4/1974 | Fletcher et al. | |
| 4,593,112 | 6/1986 | Takamizawa et al. | 556/480 |
| 4,748,262 | 5/1988 | Ishihara et al. | 556/480 |
| 5,068,386 | 11/1991 | Shirahata et al. | 556/480 |

OTHER PUBLICATIONS

Organometallic Compounds, Methuen & Co. Ltd, London, UK, vol. 1, pp. 76–103 (1967) Coates et al.
Encyclopedia of Chem Tech, The Interscience Enc. Inc., NY, NY, vol. 10, 721–734 (1966) Kirk & Othmer.
Organic Synthesis, Turke et al. vol. 27, 7–8 (1947).
Grignard Reactions of Nonmetallic Substances Prentice--Hall, Inc., NY, 1954, pp. 1306–1331.

*Primary Examiner*—Paul F. Shaver
*Attorney, Agent, or Firm*—William F. Boley

[57] ABSTRACT

A one-step process for preparation of organosilanes. The process comprises contacting magnesium metal with a mixture comprising an organic halide and a halosilane in a co-solvent comprising about one to 15 moles of a dialkyl ether comprising less than seven carbon atoms, per mole of the allyl chloride; and about 0.05 to less than two moles of a liquid aromatic hydrocarbon solvent per mole of the dialkyl ether; at a temperature within a range of about 5° C. to 200° C.

20 Claims, No Drawings

1

PROCESS FOR PREPARATION OF ORGANOSILANES

BACKGROUND OF INVENTION

The present invention is a one-step Grignard-type process for preparation of organosilanes. The process comprises contacting magnesium metal with a mixture comprising an organic halide and a halosilane in a co-solvent comprising about one to 15 moles of a dialkyl ether comprising less than seven carbon atoms, per mole of the organic halide; and about 0.05 to less than two moles of a liquid aromatic hydrocarbon solvent per mole of the dialkyl ether; at a temperature within a range of about 5° C. to 200° C. The present inventors have found that the presence of the co-solvent comprising the dialkyl ether and the liquid aromatic hydrocarbon at the described molar ratios provides for a product slurry that stirs and flows easily. These characteristics of the product slurry improve mass transfer and heat transfer during conduct of the process and allow for easier separation of the organosilane from the product slurry. Conduct of the present process in the co-solvent provides for improved ratios of the desired organosilane to by-products and improved recovery of product from the resultant slurry. Furthermore, the use of the co-solvent allows the process to be run as a continuous process. The process can be self initiating when run within the described mole ratios of liquid aromatic hydrocarbon solvent to dialkyl ether. The process is particularly useful for making allyl substituted organosilanes.

The reaction of organic halides with magnesium metal in the presence of oxygenated solvents such as dialkyl ethers to form reactive complexes typically referred to as Grignard reagents is well known. The production and reactions of Grignard reagents has been the subject of books and numerous review articles. Such reviews are provided, for example, in Coates et al., *ORGANOMETALLIC COMPOUNDS*, Vol. 1, p. 76–103, (1967), Methuen and Co. LTD, London, U.K.; and in Kirk and Othmer, *ENCYCLOPEDIA OF CHEMICAL TECHNOLOGY*, Vol. 10, 721–734 (1966), The Interscience Encyclopedia, Inc., NY, N.Y. The structure of the Grignard reagent has not been determined with certainty. However, it is generally believed that the Grignard reagent exists as a complex in solution and that solvent can play a critical role in such complex formation. The unpredictable effect of solvent on the formation and reactivity of Grignard reagents is discussed in the above cited review articles.

The preparation of organic compounds, such as 1,5-hexadiene, by a process using a Grignard reagent as an intermediate is known. For example, Turk et al., *Organic Synthesis*, Vol. 27, 7–8, 1947, teach a process for preparing 1,5-hexadiene by the reaction of allyl chloride in anhydrous ether with magnesium turnings. Turk et al. teach that this reaction results in the formation of a thick slurry which becomes unstirrable. This unstirrable slurry is then treated with a hydrochloric acid solution until the magnesium chloride by-product is in solution and the slurry becomes sufficiently fluid to be stirred.

Such processes as taught by Turk et al. are not generally acceptable as a commercial process. The formation of the non-stirrable slurry during conduct of the reaction can cause reduced mass transfer and heat transfer and therefore reduced yield. Furthermore, the nature of the slurry makes it necessary to treat the slurry in an additional step with a reagent to solubilize the slurry to allow isolation of the product. Typically, a major portion of the product is trapped within the non-stirrable slurry. In addition, the non-flowable nature of the slurry does not allow for the reaction to be run as a continuous process.

It is an objective of the present invention to provide a one-step process for preparing organosilanes using a Grignard type reagent as an intermediate, where the process avoids many of the above discussed problems with Grignard type processes by creating a reaction mixture slurry that is flowable and easily stirred. Thus, mass transfer and heat transfer can be improved in the reaction mixture providing for improved yield of organosilane. In addition, the formation of a slurry that is flowable can allow for the conduct of the process as a continuous process. No additional step is necessary to solubilize the slurry to make it flowable and allow for recovery of the organosilane.

The present inventors have found that when an organic halide is contacted with magnesium in the presence of a halosilane and a co-solvent comprising a dialkyl ether comprising less than seven carbon atoms and 0.05 to less than 2 moles of a liquid aromatic hydrocarbon solvent per mole of the dialkyl ether, the resulting slurry is flowable and easily stirred. Furthermore yields of the organosilane are improved due to, for example, improved ratios of the organosilane to by-products and the ability to recover the product from the slurry. The flowable nature of the resulting slurry allows the process to be run as a continuous process.

Richards et al., U.S. Pat. No. 3,080,324, teach that an oxygenated solvent and a liquid hydrocarbon can be used as a reaction medium in the preparation of a Grignard reagent. Richards et al. do not teach that their co-solvent system is useful in subsequent reactions of the Grignard reagent with halosilanes.

Fletcher et al., U.S. Pat. No. 3,801,558, teach that advantages can be realized when the reducing agent used in preparing a magnesium-reduced catalyst is an organomagnesium Grignard reagent prepared in a hydrocarbon solvent medium containing a controlled amount of a complexing agent for the Grignard reagent such as dialkyl ether. The reported advantage is that the Grignard reagent may be more soluble in hydrocarbon solvents at ambient temperature. Fletcher et al. report the use of the Grignard as a reducing agent for titanium trichloride in a process for making a catalyst useful in polymerizing alpha-olefins.

The reaction of Grignard reagents with halosilanes is well known and many such reactions are described in Kharash et al., *Grignard Reactions of Nonmetallic Substances*, Prentice-Hall, Inc., New York, 1954, p. 1306–1331.

Takamizawa et. al., U.S. Pat. No. 4,593,112, teach a tert-hydrocarbyl silyl compound can be synthesized by reacting a tert-hydrocarbylmagnesium halide as a Grignard reagent with a silane compound having at least one silicon-bonded hydrogen atom and at least one silicon-bonded halogen atom simultaneously in a molecule in a suitable organic solvent. Takamizawa et al. suggest that the solvent may be a mixture of an ether and an aromatic hydrocarbon solvent.

SUMMARY OF INVENTION

The present invention is a one-step process for preparation of organosilanes. The process comprises contacting magnesium metal with a mixture comprising an organic halide and a halosilane in a co-solvent comprising about one to 15 moles of a dialkyl ether comprising less than seven carbon atoms, per mole of the allyl chloride; and about 0.05 to less than two moles of a liquid aromatic hydrocarbon solvent per mole of the dialkyl ether; at a temperature within a range of about 5° C. to 200° C. The present inventors have found that the presence of the co-solvent comprising the dialkyl ether and the liquid aromatic hydrocarbon within the described molar ratio provides for a product slurry that stirs and flows easily. These characteristic of the product slurry improve mass transfer and heat transfer during conduct of the process and allow for easier separation of the organosilane from the product slurry. Conduct of the present process in the co-solvent provides for improved ratios of the desired organosilane to by-products and improved recovery of product from the resultant slurry. Furthermore, the use of the co-solvent allows the process to be run as a continuous process. The process can be self initiating when run within the described mole ratios of liquid aromatic hydrocarbon to dialkyl ether. The process is particularly useful for making allyl substituted organosilanes.

DESCRIPTION OF INVENTION

The present invention is a one-step process for the preparation of organosilanes. The process comprises contacting magnesium metal with a mixture comprising an organic halide described by formula

a halosilane described by formula

and a co-solvent comprising one to 15 moles of a dialkyl ether comprising less than seven carbon atoms, per mole of the organic halide, and about 0.05 to two moles of a liquid aromatic hydrocarbon solvent per mole of the dialkyl ether; at a temperature within a range of about 5° C. to 200° C.; where each $R^1$ and $R^2$ is an independently selected hydrocarbon group comprising one to about 12 carbon atoms, a=0 to 3, b=0 to 3, a+b=0 to 3, and X is selected from a group consisting of chlorine and bromine atoms.

The present invention is a one-step process for the preparation of organosilanes. By "one-step" it is meant that it is not necessary to isolate an intermediate Grignard type reagent in the process and further react this Grignard type reagent with the halosilane to form the organosilane. Furthermore, it is not necessary to conduct a separate solubilization step on the resulting product slurry to facilitate recovery of the organosilane.

The process comprises reacting magnesium metal with an organic halide in the presence of a halosilane and a co-solvent mixture. The method of making the magnesium metal and the physical form of the magnesium metal can be any of those known in the art. The magnesium metal can be in the form of powder, chips, and shavings. A preferred form of magnesium metal is in the form of shavings.

Contact of the magnesium metal with the organic halide can be effected in standard type reactors suitable for running Grignard type reactions. The reactor can be of a batch type, semi-batch, or continuous type. A preferred reactor is a continuous-type reactor. The environment in which the present process is run should be inert. Therefore, in a preferred process the reactor is purged and blanketed with an inert gas such as, for example, nitrogen or argon.

Typically the magnesium metal and halosilane are added to the reactor containing the co-solvent mixture and the organic halide in additional co-solvent mixture is then fed to the reactor at a controlled rate. The mole ratio of magnesium to organic halide fed to the reactor is not critical and can be varied within wide limits. In a batch process it is preferred that the mole ratio of magnesium to organic halide provide organic halide in sufficient excess to ensure essentially total conversion of the magnesium to magnesium salts. When the present process is conducted as a continuous process, the magnesium metal is typically present in excess in relation to the organic halide fed to the reactor. In such a case, the rate of feed of organic halide and halosilane to the reactor can be controlled to assure acceptable levels of conversion of the organic halide to the organosilane and minimal presence of unreacted allyl magnesium halide complexes. The halosilane feed may be split, with a portion being added after the magnesium bed to insure complete reaction of the organic magnesium halide complex. Any excess organic halide and halosilane can be recovered and recycled to the process.

Organic halides useful in the present process are described by formula $R^1X$, where $R^1$ is a hydrocarbon group comprising about one to 12 carbon atoms and X is selected from a group consisting of chlorine and bromine atoms. The preferred substituent X for the organic halide is the chlorine atom. The substituent $R^1$ can be a substituted or unsubstituted hydrocarbon group comprising one to 12 carbon atoms. The substituent $R^1$ can be a saturated or unsaturated hydrocarbon group comprising one to 12 carbon atoms. $R^1$ can be, for example, alkyl, cycloalkyl, alkenyl, cycloalkenyl, aryl, and aralkyl. Specific examples of useful $R^1$ substituents include methyl, ethyl, propyl, tert-butyl, vinyl, allyl, hexenyl, pentenyl, cyclopentyl, cyclohexyl, cyclopentenyl, cyclohexenyl, phenyl, tolyl, xylyl, benzyl, gamma tolylpropyl, chloromethyl, bromomethyl, 3,3,3-trifluoropropyl, perfluoropropyl, chlorophenyl, and bromophenyl. A preferred organic halide for use in the present process is allyl chloride.

Halosilanes useful in the present process are described by formula $R^2_aH_bSiX_{4-a-b}$, where each $R^2$ is an independently selected hydrocarbon group comprising one to about 12 carbon atoms, a=0 to 3, b=0 to 3, a+b=0 to 3, and X is selected from a group consisting of chlorine and bromine atoms. The preferred substituent X for the halosilane is a chlorine atom. The substituent $R^2$ can be as described for $R^1$. Preferred is when $R^2$ is a methyl group. Preferred is when subscript a=1 to 3 and subscript b=0 or 1. The halosilane can be, for example, methyldichlorosilane, dimethyldichlorosilane, trimethylchlorosilane, and dimethylchlorosilane.

The mole ratio of organic halide to halosilane can be varied within a range of about 0.1 to 10. Preferred is when the mole ratio of organic halide to halosilane is within a range of about 0.8 to 2. A preferred process is where the magnesium is added to the process in excess to the organic halide and the halosilane is added in excess to the resulting organic magnesium halide intermediate.

The present process is conducted in the presence of a co-solvent mixture comprising a dialkyl ether comprising less than seven carbon atoms and a liquid aromatic hydrocarbon solvent. The dialkyl ether can be, for example, dimethyl ether, diethyl ether, ethylmethyl ether, and n-butylmethyl ether. The preferred ether is diethyl ether. One to fifteen moles of the dialkyl ether can be added to the present process per mole of allyl chloride. Preferred is when about three to ten moles of dialkyl ether are added to the process per mole of allyl chloride. Even more preferred is when about two to five moles of dialkyl ether are added to the process per mole of allyl chloride.

The liquid aromatic hydrocarbon solvent, can be any aromatic hydrocarbon solvent that is a liquid under process conditions. The liquid aromatic hydrocarbon solvent can be, for example, toluene, xylene, and benzene. A preferred liquid aromatic hydrocarbon solvent is toluene.

The mole ratio of the dialkyl ether to the liquid aromatic hydrocarbon is critical to the present process. The present method requires the presence of about 0.05 to less than two moles of the liquid aromatic hydrocarbon solvent per mole of the dialkyl ether. At a ratio of two moles or greater of liquid aromatic hydrocarbon solvent per mole of the dialkyl ether, the reaction of the process does not readily initiate. At a mole ratio less than about 0.05 of liquid aromatic hydrocarbon solvent per mole of the dialkyl ether, the resulting slurry becomes of a paste like consistency and may require solubilization for efficient recovery of the organosilane. It is preferred that the mole ratio of liquid aromatic hydrocarbon solvent to dialkyl ether be within a range of about 0.2 to 1.5.

The present process can be run at a temperature within a range of about 5° C. to 200° C. It is preferred that the present process be run at a temperature within a range of about 30° C. to 170° C. The pressure at which the present process is run is not critical and can be ambient to about 200 psig. A preferred pressure is within a range of from about 0 psig to 125 psig.

The product of the present process is an organosilane in a stirrable slurry. The organosilanes that can be produced by the present process are described by formula $$R^2_a H_b R^1_c SiX_{4-a-b-c},$$

where $R^1$ and $R^2$ are independently selected hydrocarbon groups comprising one to 12 carbon atoms as previously described, X is chlorine or bromine atoms as previously described, $a=0$ to 3, $b=0$ to 3, and $a+b=0$ to 3 as previously described and $c=1$ to 4. A preferred organosilane is where each $R^2$ is methyl, each X is a chlorine atom, and $a=1$ to 3. An even more preferred organosilane is where each $R^2$ is methyl, each X is a chlorine atom, $a=1$ to 3, and $R^1$ is an allyl group. Examples of preferred organosilanes include allyltrimethylsilane, allyldimethylsilane, allyldimethylchlorosilane, and diallyldimethylsilane.

In addition to the organosilane, the slurry can comprise dialkyl ether, liquid aromatic hydrocarbon solvent, magnesium halide salts, unreacted magnesium, and other solids. The organosilane can be further isolated by separating the slurry into a liquid fraction containing the organosilane and a solids fraction containing magnesium halide salts, unreacted magnesium, and other solids. Such separation can be effected by standard means for separating liquids from solids such as settling or filtration. The liquid portion comprising the organosilane in the co-solvents can be further separated by, for example, distillation to separate the co-solvents from the organosilane. The co-solvents may be recycled to the process.

The following examples are provided to illustrate the present invention and are not intended to limit the scope of the present claims.

EXAMPLE 1

(Not within the scope of the present invention.)

A series of runs were made using diethyl ether alone as solvent. Magnesium turnings (1.61 g, 0.067 mol.), diethyl ether (13 g, 0.18 mole), halosilane (0.015 mol.) as described in Table 1, and n-octane (0.15 g) as an internal standard were loaded into a 120 ml bottle and mixed. Allyl chloride (1.56 g, 0.02 mol) in 0.5 ml of diethyl ether was slowly added to the mixture. The mixture was maintained at room temperature for the reaction times (Rx Time) described in Table 1. For some runs, as indicated in Table 1, the reaction mixture was analyzed at two different times. At the end of the reaction period, the mixture was analyzed by gas chromatography using a flame ionization detector (GC-FID). The results are presented in Table 1. The halosilane used in each run is listed in the column labelled "Halosilane" and the organosilane product formed is described in the column labelled "Organosilane" The percent yield of the organosilane is described in the column labelled "% Yield" and is calculated as the mole percent of the halosilane feed converted to the organosilane. Also provided in Table 1 is the weight ratio of the organosilane to 1,5 hexadiene, a major by-product of the process. This ratio is described in the column labelled "Silane/Diene."

TABLE 1

| Diethyl Ether as Solvent in Grignard-Type Process For Preparation of Organosilanes | | | | | |
|---|---|---|---|---|---|
| Run No. | Halosilane | Rx Time (h) | Organosilane | % Yield | Silane/Diene |
| 1 | Me$_3$SiCl | 1.5 | AllylSiMe$_3$ | 60 | 10/1 |
| 2 | Me$_2$HSiCl | 1.5 | AllylSiMe$_2$H | 42 | 4/1 |
|   |   | 12 | AllylSiMe$_2$H | 78 | 4/1 |
| 3 | Me$_2$SiCl$_2$ | 1 | AllylSiMe$_2$Cl | 5 | 2.5/1 |
|   |   | 1 | Allyl$_2$SiMe$_2$ | 9 | 3.2/1 |
|   |   | 3 | AllylSiMe$_2$Cl | 12 | 3.2/1 |
|   |   | 3 | Allyl$_2$SiMe$_2$ | 29 | 3.2/1 |

The reaction products of runs 1 to 3 were of a paste like consistency.

EXAMPLE 2

A series of runs were made using a co-solvent comprising diethyl ether and toluene. Magnesium turnings (1.61 g, 0.067 mol.), halosilane (0.015 mol.) as described in Table 2, diethyl ether (13 g, 0.18 mol.), toluene (5.3 g, 0. 057 mol.), and n-octane (0.15 g) as an internal standard were loaded into a 120 ml bottle and mixed. Allyl chloride (1.56 g, 0.02 mol.) in 0.5 ml of diethyl ether was slowly added to the mixture. The mixture was maintained at room temperature for the times described in Table 2. At the end of the reaction period, the mixture was analyzed by GC-FID and the "% Yield" calculated as described in Example 1. The results are presented in Table 2.

TABLE 2

| Diethyl Ether and Toluene as Co-solvents in Grignard-Type Process For Preparation of Organosilanes | | | | | |
|---|---|---|---|---|---|
| Run No. | Halosilane | Rx Time (h) | Organosilane | % Yield | Silane/Diene |
| 1 | Me$_3$SiCl | 1 | AllylSiMe$_3$ | 60 | 15/1 |
|   |   | 10 | AllylSiMe$_3$ | 91 | 13/1 |
| 2 | Me$_2$HSiCl | 1 | AllylSiMe$_2$H | 25 | 6/1 |
|   |   | 10 | AllylSiMe$_2$H | 70 | 6.5/1 |
| 3 | Me$_2$SiCl$_2$ | 10 | AllylSiMe$_2$Cl | 11 | 2.5/1 |
|   |   | 10 | Allyl$_2$SiMe$_2$ | 20 | 2.5/1 |

The reaction product of runs 1 to 3 using the co-solvent was free flowing, with the solids readily separating from solution and being easily dispersed after several days of standing.

EXAMPLE 3

A series of runs were made using an excess of halosilane relative to allyl chloride, and a co-solvent comprising diethyl ether and toluene. Magnesium turnings (1.61 g, 0.067 mol.), trimethylchlorosilane (2.45 g, 0.023 mol. for run 1 and 2.71 g, 0.0249 mol. for run 2), diethyl ether (13 g, 0.18 mol.), toluene (2 g, 0.021 mol.), and n-octance (0.21 g) as an internal standard were loaded into a 120 ml bottle and mixed. Allyl chloride (1.56 g, 0.02 mol.) in 0.5 ml of diethyl ether was slowly added to the mixture. The mixture was maintained at room temperature for the reaction times described in Table 3. At the end of the reaction period, the reaction mixture was analyzed by GC-FID. The results are present in Table 3. In Table 3 the information under the heading "Me$_3$SiCl/Allyl-Cl" is the mole ratio of trimethylchlorosilane to allyl chloride added to the process.

TABLE 3

Effect of Excess Halosilane in Grignard-Type Process
For Preparation of Organosilanes

| Run No. | Me$_3$SiCl/Allyl-Cl | Rx Time (h) | % Yield | Silane/Diene |
|---|---|---|---|---|
| 1 | 1.15 | 0.25 | 27 | — |
|   |      | 1    | 44 | — |
|   |      | 10   | 71 | 500/1 |
| 2 | 1.25 | 1    | 48 | — |
|   |      | 6    | 60 | — |
|   |      | 10   | 70 | 500/1 |

The reaction products of runs 1 and 2 of this example were free flowing, with the solids readily separating from solution and being easily dispersed.

We claim:

1. A one-step process for preparation of organosilanes, the process comprising contacting magnesium metal with a mixture comprising an organic halide described by formula $R^1X$, a halosilane described by formula $R^2_aH_bSiX_{4-a-b}$, and a co-solvent comprising one to 15 moles of a dialkyl ether comprising less than seven carbon atoms, per mole of the organic halide, and about 0.05 to two moles of a liquid aromatic hydrocarbon solvent per mole of the dialkyl ether; at a temperature within a range of about 5° C. to 200° C.; where each R$^1$ and R$^2$ is an independently selected hydrocarbon group comprising one to about 12 carbon atoms, a=0 to 3, b=0 to 3, a+b=0 to 3, and X is selected from a group consisting of chlorine and bromine atoms.

2. A process according to claim 1, where the magnesium metal is in the form of shavings.

3. A process according to claim 1, where the magnesium metal is contacted with the mixture by directing a continuous flow of the mixture through a bed of magnesium metal.

4. A process according to claim 1, where the magnesium metal is contacted with the mixture in an inert environment.

5. A process according to claim 1, where the dialkyl ether is diethyl ether.

6. A process according to claim 1, where the mixture comprises about three to ten moles of dialkyl ether per mole of the allyl chloride.

7. A process according to claim 1, where the liquid aromatic hydrocarbon solvent is selected from a group consisting of toluene, xylene, and benzene.

8. A process according to claim 1, where the liquid aromatic hydrocarbon solvent is toluene.

9. A process according to claim 1, where the mixture comprises 0.2 to 1.5 moles of liquid aromatic hydrocarbon solvent per mole of dialkyl ether.

10. A process according to claim 1, where the liquid aromatic hydrocarbon solvent is toluene, the dialkyl ether is diethyl ether, and the mole ratio of liquid aromatic hydrocarbon solvent to dialkyl ether is within a range of about 0.2 to 1.5.

11. A process according to claim 1, where the temperature is within a range of about 30° C. to 170° C.

12. A process according to claim 1, where the liquid aromatic hydrocarbon solvent is toluene and the dialkyl ether is diethyl ether.

13. A process according to claim 1, where the organic halide is allyl chloride.

14. A process according to claim 1, where the halosilane is selected from a group consisting of trimethylchlorosilane, dimethylchlorosilane, and dimethyldichlorosilane.

15. A process according to claim 1, where the organic halide is allyl chloride and the halosilane is selected from a group consisting of trimethylchlorosilane, dimethylchlorosilane, methyldichlorosilane, and dimethyldichlorosilane.

16. A process according to claim 1, where the mole ratio of the organic halide to the halosilane is within a range of about 0.1 to 10.

17. A process according to claim 1, where the mole ratio of the organic halide to the halosilane is within a range of about 0.8 to 2.

18. A process according to claim 1, where the process is run as a continuous process, the dialkyl ether is diethyl ether, the mixture comprises about two to five mole of diethyl ether per mole of allyl chloride, the liquid aromatic hydrocarbon solvent is toluene, the mole ratio of toluene to diethyl ether in the mixture is within a range of about 0.2 to 1.5, the temperature is within a range of about 30° C. to 170° C., and the magnesium metal is contacted with the mixture at a pressure within a range from about 0 psig to 125 psig.

19. A process according to claim 14, where the magnesium metal is contacted with the mixture in an inert environment comprising nitrogen gas.

20. A process according to claim 1, where the mixture comprises about two to five moles of dialkyl ether per mole of the allyl chloride.

* * * * *